(12) United States Patent
Tummala et al.

(10) Patent No.: US 9,926,296 B2
(45) Date of Patent: Mar. 27, 2018

(54) PROCESS FOR THE PREPARATION OF POLYMORPHIC FORMS OF NILOTINIB HYDROCHLORIDE

(71) Applicant: DR. REDDY'S LABORATORIES LIMITED, Hyderabad (IN)

(72) Inventors: Arjun Kumar Tummala, Visakhapatnam (IN); Srinivas Rangineni, Mahabubnagar (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 0 days.

(21) Appl. No.: 15/502,715

(22) PCT Filed: Aug. 7, 2015

(86) PCT No.: PCT/IB2015/056015
§ 371 (c)(1),
(2) Date: Feb. 8, 2017

(87) PCT Pub. No.: WO2016/020891
PCT Pub. Date: Feb. 11, 2016

(65) Prior Publication Data
US 2017/0240528 A1   Aug. 24, 2017

(30) Foreign Application Priority Data
Aug. 8, 2014   (IN) .................... 3902/CHE/2014

(51) Int. Cl.
*C07D 401/14*   (2006.01)

(52) U.S. Cl.
CPC ........ *C07D 401/14* (2013.01); *C07B 2200/13* (2013.01)

(58) Field of Classification Search
CPC .................................. C07D 401/14
See application file for complete search history.

(56) References Cited

U.S. PATENT DOCUMENTS

| | | | |
|---|---|---|---|
| 8,227,477 B2 | 7/2012 | Sterimbaum et al. | |
| 8,580,806 B2 | 11/2013 | Manley et al. | |
| 8,592,442 B2 | 11/2013 | Sterimbaum et al. | |
| 8,703,788 B2 | 4/2014 | Reddy et al. | |
| 8,829,015 B2 | 9/2014 | Manley et al. | |
| 9,090,598 B2 | 7/2015 | Piran et al. | |
| 9,580,408 B2 | 2/2017 | Peddy et al. | |
| 2013/0210847 A1 | 8/2013 | Kompella et al. | |

FOREIGN PATENT DOCUMENTS

| | | |
|---|---|---|
| WO | 2011086541 A1 | 7/2011 |
| WO | 2012055351 A1 | 5/2012 |

OTHER PUBLICATIONS

IP.com Journal, "NLT HCI Crystalline Forms", May 26, 2009, No. IPCOM000183524D, pp. 1 to 11, vol. 9(12B)—Issue No. 14.
IP.com Journal, "Crystalline Forms of NLT HCI", Mar. 8, 2010, No. IPCOM000193749D, pp. 1 to 3, vol. 10(3B)—Issue No. 11.
IP.com Journal, "Crystalline forms of 4-methyl-N-[3-(4-methyl-1H-imidazol-1-yl)-5-(trifluoromethyl)phenyl]-3-[[4-(3-(pyridinyl)-2-pyrimidinyl]amino]-benzamide salts", Nov. 18, 2010, No. IPCOM000201702D, pp. 1 to 8, vol. 10(12A)—issue No. 18.
IP.com Journal, "Crystalline Form of 4-methyl-N-[3-(4-methyl-1H-imidazol-1-yl)-5-(trifluoromethyl)phenyl]-3  [[4-(3-pyridinyl)-2-pyrimidinyl]amino]-benzamide", Apr. 29, 2010, No. IPCOM000195326D, pp. 1 and 2, vol. 10(5A)—issue No. 25.
IP.com Journal, "Amorphous 4-methyl-N-[3-(4-methyl-1H-imidazol-1-yl)-5-(trifluoromethyl)phenyl]-3  [[4-(3-pyridinyl)-2-pyrimidinyl]amino]-benzamide salts", Jul. 1, 2010, No. 000197295, pp. 1 to 9, vol. 10(7B)—issue No. 3.
International Search Report for corresponding International Patent Application No. PCT/IB2015/056015, dated Dec. 30, 2015.
International Preliminary Report on Patentability for corresponding International Application No. PCT/IB2015/056015, dated Feb. 14, 2017.
Written Opinion for corresponding International Patent Application No. PCT/IB2015/056015, dated Dec. 30, 2015.
International Search Report for corresponding International Patent Application No. PCT/IB2014/060935, dated Dec. 31, 2014.
Written Opinion for corresponding International Patent Application No. PCT/IB2014/060935, dated Dec. 31, 2014.

*Primary Examiner* — Bruck Kifle
(74) *Attorney, Agent, or Firm* — Pergament & Cepeda LLP; Milagros A. Cepeda; Edward D. Pergament

(57) ABSTRACT

A process for preparing Nilotinib hydrochloride Form R5 and Form R6 comprises: step a) providing a solution of Nilotinib free base in acetic acid and optionally an organic solvent, step b) adding hydrochloric acid taken in an organic solvent to the solution of step a), then separating Nilotinib hydrochloride Form R5 (step c), and finally drying at about 100° C. to 150° C. to obtain Nilotinib hydrochloride Form R6.

4 Claims, 4 Drawing Sheets

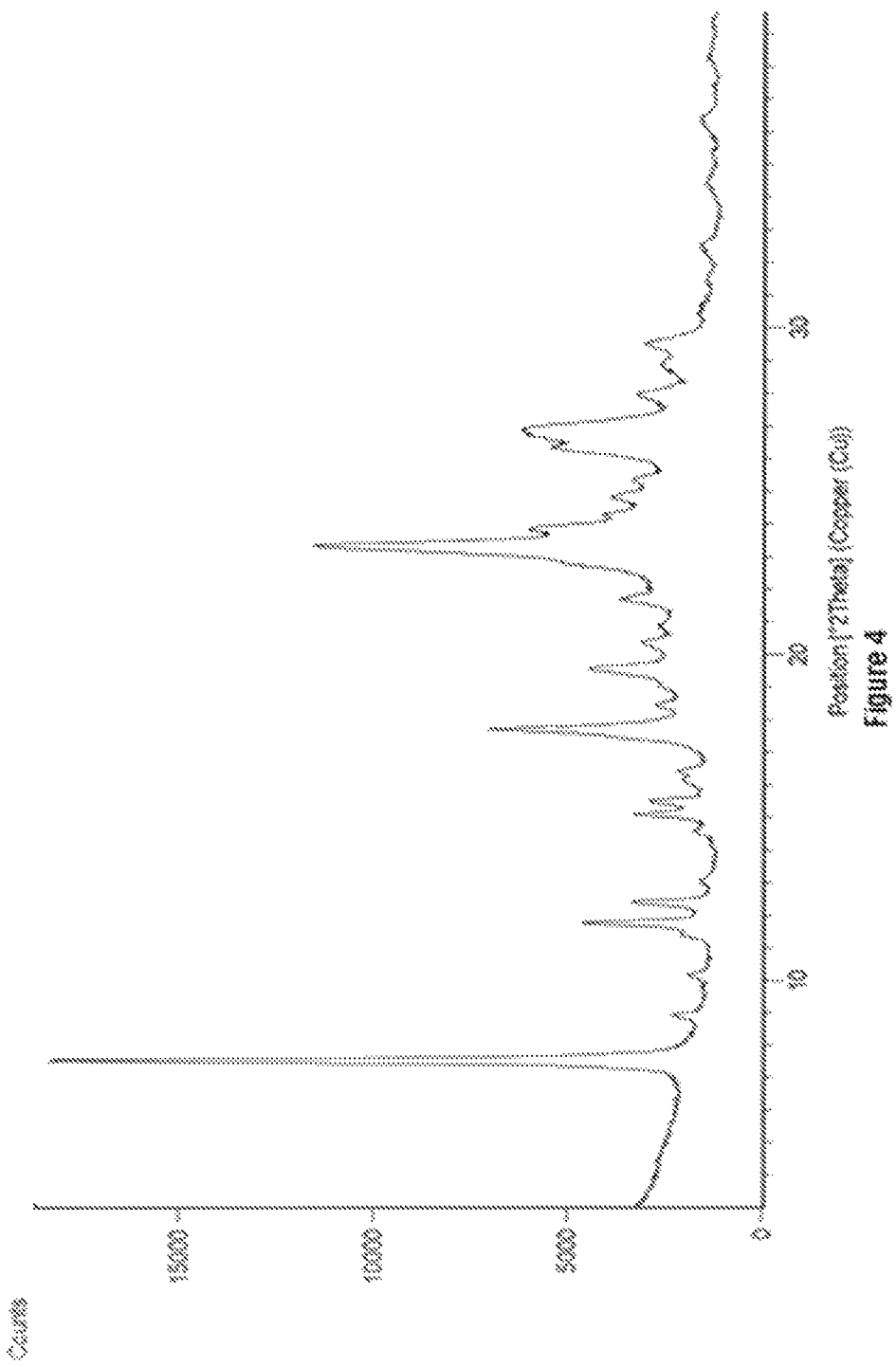

PROCESS FOR THE PREPARATION OF POLYMORPHIC FORMS OF NILOTINIB HYDROCHLORIDE

This application is a National Stage Application under 35 U.S.C. § 371 of PCT International Application No. PCT/162015/056015, filed Aug. 7, 2015, which claims the benefit of Indian Provisional Application No. 3902/CHE/2014, filed Aug. 8, 2014, all of which are hereby incorporated by reference in their entireties.

INTRODUCTION

The present invention provides process for the preparation of polymorphic forms R5 and R6 of Nilotinib hydrochloride.

BACKGROUND OF THE INVENTION

The drug compound having the adopted name "nilotinib hydrochloride" has a chemical name 4-methyl-N-[3-(4-methyl-1H-imidazol-1-yl)-5-(trifluoromethyl) phenyl]-3-[[4-(3-pyridinyl)-2-pyrimidinyl]amino]-benzamide monohydrochloride, and is structurally represented by Formula I.

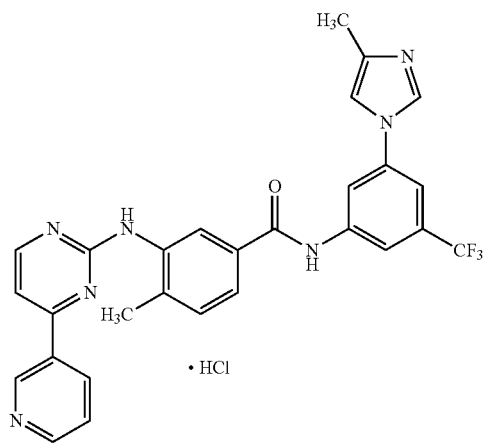

Formula I

Nilotinib hydrochloride is a kinase inhibitor, approved as nilotinib hydrochloride monohydrate, sold using the trade name Tasigna®, in the form of capsule for the treatment of chronic phase and accelerated phase Philadelphia chromosome positive chronic myelogenous leukemia (CML) in adult patients resistant to or intolerant to prior therapy that included imatinib.

International application publication No. WO2007/015871 A1 describes salts of 4-methyl-N-[3-(4-methyl-1H-imidazol-1-yl)-5-(trifluoromethyl)phenyl]-3-[[4-(3-pyridinyl)-2-pyrimidinyl] amino]-benzamide, wherein the salt is a hydrochloride salt, hydrochloride monohydrate, monophosphate salt, diphosphate salt, sulfate salt, methanesulfate salt, ethanesulfonate salt, benzene sulfonate salt, p-toluene sulfonate salt, citrate salt, fumarate salt, malonate salt, malate salt, tartrate salt, etc., their polymorphic forms and process for the preparation thereof. Further, it also discloses the crystalline forms of nilotinib hydrochloride designated as Form A and Form B, process for their preparation and process for the preparation of nilotinib hydrochloride monohydrate.

International application publication No. WO2007/015870 A2 describes substantially pure crystalline forms of nilotinib hydrochloride designated as Form A, Form A', Form A", Form B, Form B', Form $S_B$, Form $S_{B'}$, Form C, Form C', Form $S_C$, Form D, Form $S_E$, mixture of Form B and Form D, and amorphous form of Nilotinib hydrochloride. Further, it also discloses substantially pure crystalline forms A and B of Nilotinib free base and substantially pure crystalline forms A and B of Nilotinib sulfate salt.

International application publication No. WO2010/054056 A2 describes polymorphic forms of nilotinib hydrochloride designated as forms T1, T2, T3, T4, T5, T6, T7, T8, T9, T10, T11, T12, T13, T14, T15 T16, T17, T18, and T19. Further, it also describes solid dispersion of nilotinib hydrochloride in combination with a pharmaceutically suitable excipient.

International application publication No. WO2011/163222 describes polymorphic forms of nilotinib hydrochloride designated as forms T20, T27, T28 and T29.

International application publication No. WO2011/086541 A1 describes a crystalline form of nilotinib hydrochloride monohydrate having an X-ray diffraction pattern comprising peaks at 5.70, 7.56, 9.82, 15.01, 17.31 and 27.68±0.2 degrees 2-theta and process for its preparation.

International application publication No. WO2012/055351 A1 describes a crystalline form of nilotinib hydrochloride monohydrate having an X-ray diffraction pattern comprising peaks at 4.987, 8.430, 11.309, 14.403, 17.219, 19.225 and 25.544 degrees 2-theta and process for its preparation.

International application publication No. WO2012/070062 A2 describes nilotinib hydrochloride crystalline form H1, characterized by peaks in the powder x-ray diffraction spectrum having 2-theta angle positions at about 8.6, 11.4, 13.2, 14.3, 15.5, 17.3, 19.2 and 25.3±0.2 degrees and process for its preparation.

US application publication No. 2013/0210847 A1 describes nilotinib hydrochloride dihydrate, characterized by peaks in the powder X-ray diffraction pattern at 4.3, 8.7, 9.5, 11.3, 13.2, 14.4, 17.3, 18.6, 19.3, 20.8, 22.2 and 25.3 degrees 2-theta (±0.1 degrees 2-theta).

IP.com Journal (2010), 10(3B), 11 describes the crystalline forms T24, T25, and T26 of nilotinib hydrochloride and process for their preparation.

IP com Journal (2010), 10(12A), 18 describes the crystalline forms of nilotinib hydrochloride designated as Forms T19 and T20 and process for their preparation.

IP.com Journal (2009), 9(12B), 14 describes the nilotinib hydrochloride crystalline forms T2-T6, T9 and T11-T13 and process for their preparation.

IP.com Journal (2010), 10(5A), 25 describes the nilotinib hydrochloride crystalline form T5 and process for its preparation.

IP.com Journal (2010), 10(7B), 3 describes a method for the preparation of the 4-methyl-N-[3-(4-methyl-1H-imidazol-1-yl)-5-(trifluoromethyl)phenyl]-3-[[4-(3-pyridinyl)-2-pyrimidinyl]amino]benzamide salts in amorphous form.

The discovery of new polymorphic forms and/or solvates of a drug or a pharmaceutically useful compound provide opportunity to improve the characteristics of a pharmaceutically acceptable dosage form of the drug with a targeted release profile or other desired characteristics.

The international publication number WO2014/174456A2 discloses the forms R5 and R6 of nilotinib hydrochloride.

SUMMARY OF THE INVENTION

In an aspect, the present invention provides a process for preparing a crystalline nilotinib hydrochloride Form R5, characterized by data selected from the group consisting of: an X-ray powder diffraction pattern with peaks at about 6.27±0.2, 15.44±0.2, 16.15±0.2, 24.07±0.2 and 26.11±0.2 degrees 2-theta; an X-ray powder diffraction pattern with peaks at about 11.26±0.2, 12.24±0.2, 12.54±0.20, 18.81±0.2 and 27.94±0.2 degrees 2-theta; an X-ray powder diffraction pattern substantially as depicted in FIG. 1, by reacting nilotinib free base with hydrochloric acid in a mixture of acetic acid and an organic solvent.

In an aspect, the present application provides a process for preparing a crystalline nilotinib hydrochloride Form R6, characterized by X-ray powder diffraction pattern having peaks at about 7.56±0.2, 10.16±0.2, 12.42±0.2, 20.32±0.2 and 27.97±0.2 degrees 2-theta; an X-ray powder diffraction pattern with peaks at about 8.93±0.2, 11.76±0.2, 15.53±0.2, 17.71±0.2, 19.57±0.2, 21.72±0.2 and 23.40±0.2 degrees 2-theta; an X-ray powder diffraction pattern substantially as depicted in FIG. 2, by heating crystalline Form R5 at a temperature of about 100° C. to about 150° C.

BRIEF DESCRIPTION OF THE DRAWINGS

FIG. 2 and FIG. 4 illustrate a characteristic X-ray powder diffraction pattern of nilotinib hydrochloride Form R6.

DETAILED DESCRIPTION

Figure 1:
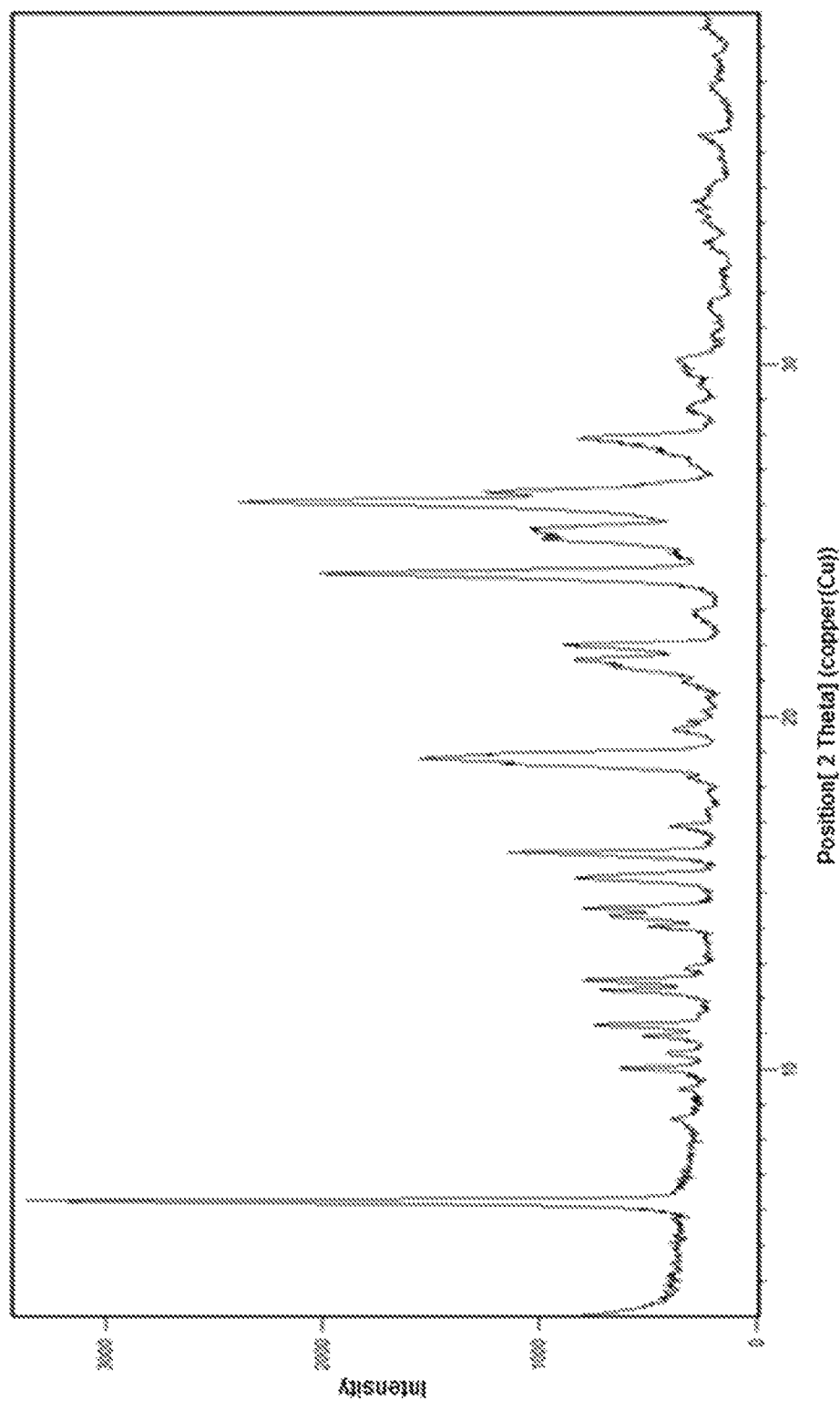
FIG. 1 and FIG. 3 illustrate a characteristic X-ray powder diffraction pattern of nilotinib hydrochloride Form R5.

In an aspect, the present invention provides a process for preparing crystalline nilotinib hydrochloride Form R5, characterized by data selected from the group consisting of: an X-ray powder diffraction pattern with peaks at about 6.27±0.2, 15.44±0.2, 16.15±0.2, 24.07±0.2 and 26.11±0.2 degrees 2-theta; an X-ray powder diffraction pattern with peaks at about 11.26±0.2, 12.24±0.2, 12.54±0.20, 18.81±0.2 and 27.94±0.2 degrees 2-theta; an X-ray powder diffraction pattern substantially as depicted in FIG. 1, by reacting nilotinib free base with hydrochloric acid in a mixture of acetic acid and an organic solvent.

In an aspect, a process for preparing nilotinib hydrochloride Form R5 comprising the steps of:
 a) providing a solution of nilotinib free base in acetic acid and an organic solvent;
 b) adding hydrochloric acid to the solution obtained in step a); and
 c) separating nilotinib hydrochloride Form R5.

The process comprises mixing nilotinib free base in acetic acid and an organic solvent at a suitable temperature until nilotinib free base is dissolved completely; optionally, making the solution particle free; adding hydrochloric acid to the solution; optionally adding an organic solvent to the above solution to assist precipitation; optionally adding the seed crystals of Form R5. The crystalline Form R5 may be separated, e.g., by filtration, decantation, centrifugation, gravity filtration, suction filtration or any other suitable techniques for the isolation of solids.

Suitable organic solvent include esters of alkanoic acid such as methyl acetate, ethyl acetate, propyl acetate, butyl acetate, methyl propanoate, ethyl propanoate, methyl butanoate, ethyl butanoate and the like.

In a further aspect, a process for preparing nilotinib hydrochloride Form R5 comprising the steps of:
 a) providing a solution of nilotinib free base in acetic acid;
 b) adding hydrochloric acid taken in an organic solvent to the solution obtained in step a);
 c) separating nilotinib hydrochloride Form R5.

The process comprises mixing nilotinib free base in acetic acid at a suitable temperature until nilotinib free base is dissolved completely; optionally, making the solution particle free; adding hydrochloric acid to the solution by dissolving in an suitable organic solvent; optionally adding an organic solvent to the above mixture to assist precipitation; optionally adding the seed crystals of Form R5. The crystalline Form R5 may be separated, e.g., by filtration, decantation, centrifugation, gravity filtration, suction filtration or any other suitable techniques for the isolation of solids.

Suitable organic solvent in step b) may be selected from esters of alkanoic acid such as methyl acetate, ethyl acetate, propyl acetate, butyl acetate, methyl propanoate, ethyl propanoate, methyl butanoate, ethyl butanoate and the like.

Figure 2:
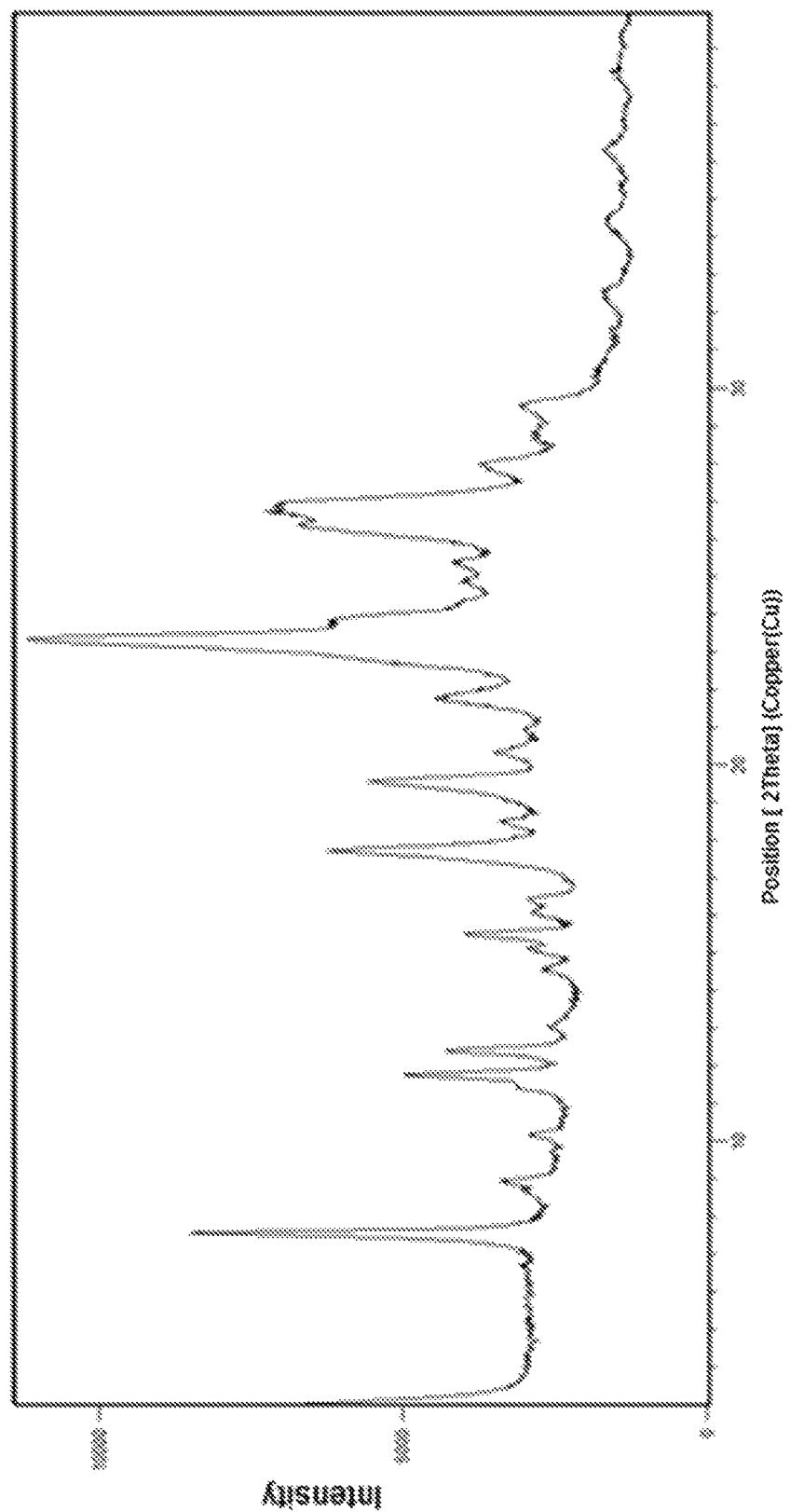
Figure 3:
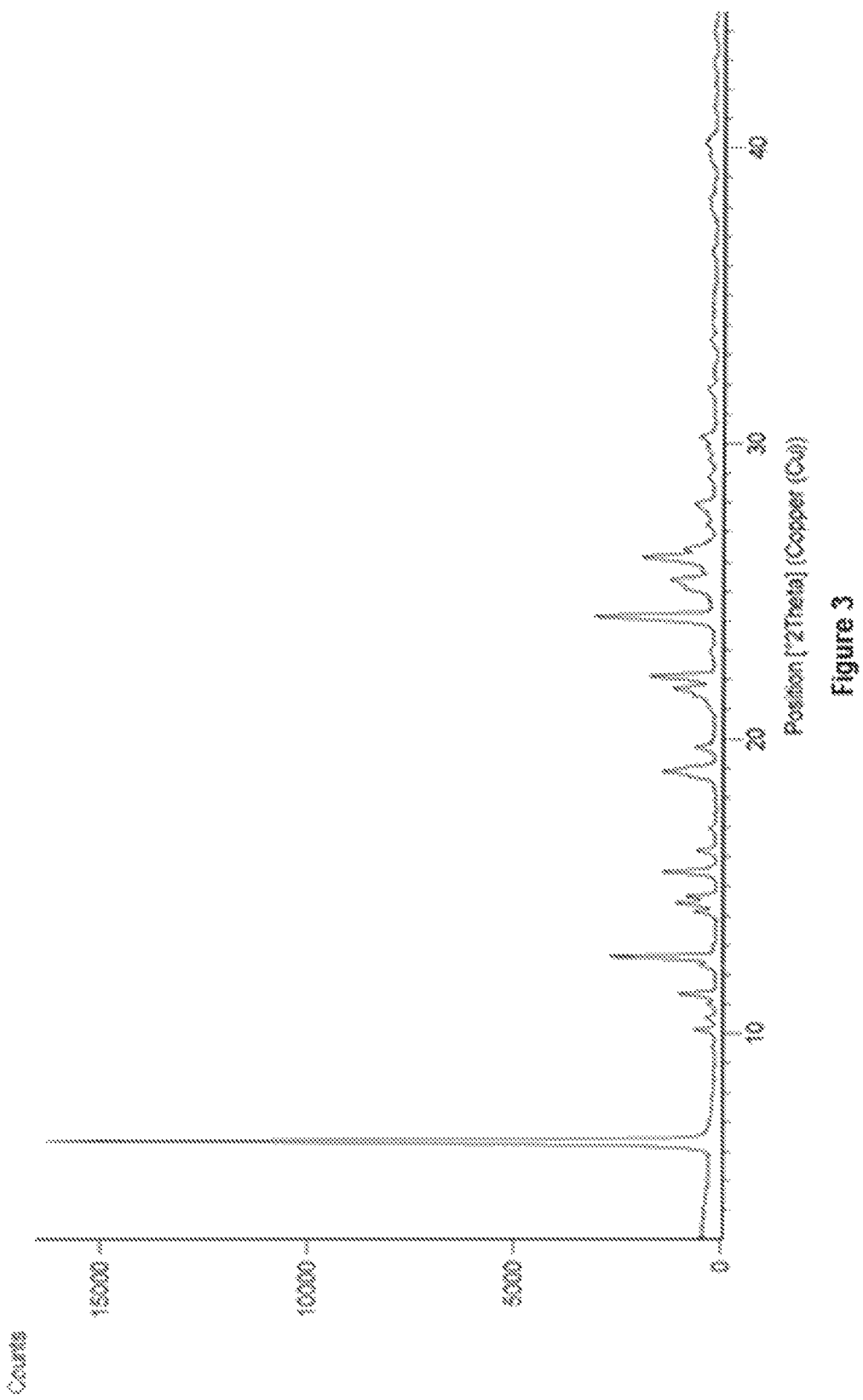

In a further aspect, the present application provides a process for preparing crystalline nilotinib hydrochloride Form R6, characterized by X-ray powder diffraction pattern having peaks at about 7.56±0.2, 10.16±0.2, 12.42±0.2, 20.32±0.2 and 27.97±0.2 degrees 2-theta; an X-ray powder diffraction pattern with peaks at about 8.93±0.2, 11.76±0.2, 15.53±0.2, 17.71±0.2, 19.57±0.2, 21.72±0.2 and 23.40±0.2 degrees 2-theta; an X-ray powder diffraction pattern substantially as depicted in FIG. 2, by heating crystalline Form R5 at a temperature of about 100° C. to about 150° C.

A process for preparing nilotinib hydrochloride Form R6 comprising the steps of:
 a) providing a solution of nilotinib free base in acetic acid and an organic solvent;
 b) adding hydrochloric acid to the solution obtained in step a);
 c) separating nilotinib hydrochloride Form R5; and
 d) drying at a temperature of about 100° C. to about 150° C. to obtain nilotinib hydrochloride Form R6.

The process comprises mixing nilotinib free base in acetic acid and an organic solvent at a suitable temperature until nilotinib free base is dissolved completely; optionally, making the solution particle free; adding hydrochloric acid to the solution; optionally adding an organic solvent to assist precipitation; optionally adding the seed crystals of Form R5 or Form R6. The crystalline Form R5 may be separated, e.g., by filtration, decantation, centrifugation, gravity filtration, suction filtration or any other suitable techniques for the isolation of solids. Crystalline Form R5 is dried at about 100° C. to about 150° C.

Suitable organic solvent in step a) may be selected from esters of alkanoic acid such as methyl acetate, ethyl acetate, propyl acetate, butyl acetate, methyl propanoate, ethyl propanoate, methyl butanoate, ethyl butanoate and the like.

Drying may be carried out in a gravity oven, tray dryer, vacuum oven, Büchi® Rotavapor®, air tray dryer, vacuum tray dryer, Roto Cone Vacuum Dryer, fluidized bed dryer, spin flash dryer, flash dryer, and the like. In an embodiment, the drying may be carried out at atmospheric pressure, under reduced pressures or by applying nitrogen/hot nitrogen. In an embodiment, the drying may be carried out at a temperature of about 120° C., at a temperature of about 115° C., at a temperature of about 110° C. or at a temperature of about 105° C. The drying may be carried out for any time periods required for obtaining a desired quality, such as from about 15 minutes to several hours, or longer.

A process for preparing nilotinib hydrochloride Form R6 comprising the steps of:
 a) providing a solution of nilotinib free base in acetic acid;
 b) adding hydrochloric acid taken in an organic solvent to the solution obtained in step a);
 c) separating nilotinib hydrochloride Form R5; and d) drying at a temperature of about 100° C. to about 150° C. to obtain nilotinib hydrochloride Form R6.

The process comprises mixing nilotinib free base in acetic acid at a suitable temperature until nilotinib free base is dissolved completely; optionally, making the solution particle free; adding hydrochloric acid to the solution in an suitable organic solvent; optionally adding an organic solvent to the above mixture to assist precipitation; optionally adding the seed crystals of Form R5 or Form R6. The crystalline Form R5 may be separated, e.g., by filtration, decantation, centrifugation, gravity filtration, suction filtration or any other suitable techniques for the isolation of solids. Crystalline Form R5 is dried at about 100° C. to about 150° C.

Suitable organic solvent in step b) may be selected from esters of alkanoic acid such as methyl acetate, ethyl acetate, propyl acetate, butyl acetate, methyl propanoate, ethyl propanoate, methyl butanoate, ethyl butanoate and the like.

Drying may be carried out in a gravity oven, tray dryer, vacuum oven, Büchi® Rotavapor®, air tray dryer, vacuum tray dryer, Roto Cone Vacuum Dryer, fluidized bed dryer, spin flash dryer, flash dryer, and the like. In an embodiment, the drying may be carried out at atmospheric pressure, under reduced pressures or by applying nitrogen/hot nitrogen. In an embodiment, the drying may be carried out at a temperature of about 120° C., at a temperature of about 115° C., at a temperature of about 110° C. or at a temperature of about 105° C. The drying may be carried out for any time periods required for obtaining a desired quality, such as from about 15 minutes to several hours, or longer.

In an aspect, the present invention provides a process for preparing nilotinib hydrochloride Form R6 comprising the steps of:

a) obtaining a suspension of nilotinib hydrochloride in acetic acid;
b) adding an anti-solvent to the suspension of step a);
c) maintaining the reaction mixture of step b) at a temperature of about 0° C. to about 50° C.;
d) isolating the obtained crystalline compound of Form R5; and
e) drying at a temperature of about 100° C. to about 120° C. to obtain nilotinib hydrochloride Form R6.

In the above process step b) involves adding a suitable anti-solvent to the suspension of step a). The suitable anti-solvent may be selected from ethyl acetate, dimethyl carbonate and cyclopentyl methyl ether and methyl tert-butyl ether.

Optionally, seed crystals of Form R5 or Form R6 may be added to the reaction mixture of step b). The seed crystals of Form R5 or Form R6 may be added prior to the addition of anti-solvent and before to step c).

Step d) involves isolating nilotinib hydrochloride Form R5. The crystalline nilotinib hydrochloride Form R5 is isolated in a manner known per se, and depending on the solvent used, which include, but not limited to filtration by gravity or by suction/vacuum, distillation, centrifugation, or slow evaporation or the like. In an embodiment, nilotinib hydrochloride Form R5 may be isolated by filtration under vacuum, suction drying at a temperature of about 25° C. to about 35° C. and/or drying at a temperature of less than about 45° C. Step e) involves drying the product at a temperature of about 100° C. to about 120° C. to obtain nilotinib hydrochloride Form R6.

Drying may be suitably carried out using any equipment such as a gravity oven, tray dryer, vacuum oven, Büchi® Rotavapor®, air tray dryer, vacuum tray dryer, Roto Cone Vacuum Dryer, fluidized bed dryer, spin flash dryer, flash dryer, and the like. In an embodiment, the drying may be carried out at atmospheric pressure, under reduced pressures or by applying nitrogen/hot nitrogen. In an embodiment, the drying may be carried out at a temperature of about 120° C., at a temperature of about 115° C., at a temperature of about 110° C. or at a temperature of about 105° C. The drying may be carried out for any time periods required for obtaining a desired quality, such as from about 15 minutes to several hours, or longer.

Certain specific aspects and embodiments of the present invention will be explained in more detail with reference to the following examples, which are provided only for purposes of illustration and should not be construed as limiting the scope of the present application in any manner.

EXAMPLES

Example 1: Preparation of Nilotinib Hydrochloride Form R5

3.0 g of nilotinib free base, 15.0 mL of acetic acid and 15.0 mL of ethyl acetate were charged into a round bottom flask and stirred at 28° C. 0.55 g of concentrated hydrochloric acid was added to the above flask at 28° C. and maintained for 1 hour. 15.0 mL of ethyl acetate was added to above reaction flask and stirred for 1 hour. The reaction mass was filtered using a suction pump and washed with 10 mL of ethyl acetate under nitrogen atmosphere at 28° C. to obtain the title compound.

Example 2: Preparation of Nilotinib Hydrochloride Form R6

3.0 g of nilotinib hydrochloride Form R5 was dried in air tray dryer at 110° C. for 6 hours to obtain the titled compound.

Example 3: Preparation of Nilotinib Hydrochloride Form R6

Nilotinib free base (50.0 g) and acetic acid (400 mL) were charged into a round bottom flask and stirred at 25-30° C. The contents were filtered over Hyflow and washed with acetic acid (100 mL). The filtrate was transferred into a reactor and ethyl acetate HCl (36.5 mL, Assay 10.92%) was added to the above reactor at 25-30° C. and maintained for 1 hour at 30-35° C. 0.6 g of seed material (Form R6) was added and stirred. Ethyl acetate (1000 mL) was added to the above reaction flask at 30-35° C. and stirred for 1 hour. The reaction mass was filtered at 25-30° C. on pressure nutsche filter under nitrogen atmosphere. The obtained material was dried in rotavapour at 115° C. under reduced pressure to obtain the title compound.

Example 4: Preparation of Nilotinib Hydrochloride Form R6

Nilotinib free base (60.0 g) was dissolved in acetic acid (500 mL) at 25-30° C. The contents were filtered over Hyflow and washed with acetic acid (100 mL). The filtrate was transferred into a reactor and ethyl acetate HCl (43.9 mL, Assay 10.92%) was added to the above reactor at 25-30° C. and maintained for 1 hour at 30-35° C. 0.6 g of seed material (Form R6) was added and stirred. Ethyl acetate (1200 mL) was added to the above reaction flask at 30-35° C. and stirred for 1 hour. The reaction mass was filtered at 25-30° C. on pressure nutsche filter under nitrogen atmosphere. The obtained material was dried in rotavapour at 115° C. under reduced pressure to obtain the title compound.

Example 5: Preparation of Nilotinib Hydrochloride Form R5

Nilotinib HCl (1 g) and acetic acid (5 mL) were charged into a round bottom flask and stirred at 25-35° C. Dimethyl Carbonate (50 mL) was added and the mixture was stirred at 25-30° C. for 1-2 hours. The obtained material was filtered on Buchner funnel under reduced pressure and suck dried to obtain the title compound.

Example 6: Preparation of Nilotinib Hydrochloride Form R5

Nilotinib HCl (1 g) and acetic acid (5 mL) were charged into a round bottom flask and stirred at 25-35° C. Ethyl acetate (50 mL) was added and the mixture was stirred at 25-30° C. for 1-2 hours. The obtained material was filtered on Buckner funnel under reduced pressure and suck dried to obtain the title compound.

Example 7: Preparation of Nilotinib Hydrochloride Form R6

Nilotinib HCl (10 g) and acetic acid—cyclopentyl methyl ether (100 mL; 1:1) were charged into a round bottom flask and stirred at 25-35° C. Cyclopentyl methyl ether (100 mL) was added and the mixture was stirred at 25-30° C. for 1-2 hours. The obtained material was filtered on Pressure Nutsche filter (PNF) under nitrogen atmosphere and press dried to obtain Form R5. The Form R5 was dried in air tray dryer (ATD) for 5-6 hours at 110-120° C. to obtain the title compound.

Example 8: Preparation of Nilotinib Hydrochloride Form R6

Nilotinib HCl (8 g) and acetic acid (28 mL) were charged into an EasyMax reactor and stirred at 25-35° C. The contents were heated to 45-50° C. and added slowly cyclopentyl methyl ether (28 mL). The contents were cooled to 20-25° C. and cyclopentyl methyl ether (50 mL) was further added. The contents were filtered and suck dried for 15 minutes. The obtained material was dried in air tray dryer (ATD) at 110-120° C. to obtain the title compound.

Example 9: Preparation of Nilotinib Hydrochloride Form R6

Nilotinib HCl (2 g) and acetic acid (20 mL) were charged into an EasyMax reactor and stirred at 25-35° C. to obtain a clear solution. The solution was further stirred at 25-30° C. until the solid separates out. Methyl tertiary butyl ether (50 mL) was added and the mixture was stirred at 25-30° C. for 10-12 hours. The obtained material was filtered and suck dried. The material was further dried in air tray dryer (ATD) at 110-120° C. to obtain the title compound.

Example 10: Preparation of Nilotinib Hydrochloride Form R6

Nilotinib HCl (2 g) and acetic acid (20 mL) were charged into an EasyMax reactor and stirred at 25-35° C. to obtain a clear solution. The contents were stirred at 25-30° C. for 4-5 hours and solid separated out. Cyclopentyl methyl ether (50 mL) was added to the obtained solid and slurred for 12-14 hours. The obtained solid was filtered on Buckner funnel and suck dried for 15-20 minutes. The material was unloaded and dried in air tray dryer at 110-120° C. to obtain the title compound.

Example 11: Preparation of Nilotinib Hydrochloride Form R6

Nilotinib HCl (2 g) and acetic acid (10 mL) were charged in an RBF and stirred at 25-35° C. Methyl tertiary butyl ether (30 mL) was added and the mixture was stirred at 25-30° C. for 2-3 hours. The obtained material was filtered on Buckner funnel and suck dried. The material was unloaded and dried in air tray dryer (ATD) at 110-120° C. to obtain the title compound.

Example 12: Preparation of Nilotinib Hydrochloride Form R6

Acetic acid (25 mL) and ethyl acetate (25 mL) were taken in an RBF. Nilotinib HCl (5 g) was added to the above flask at 25-30° C. and stirred for 2-3 hours. The contents were filtered on Pressure Nutsche filter (PNF) under nitrogen atmosphere and press dried for 15-20 minutes. The obtained material was unloaded and dried in air tray dryer (ATD) at 110-120° C. to obtain the title material.

Example 13: Preparation of Nilotinib Hydrochloride Form R6

Acetic acid (120 mL) was charged into a clean and dry reactor at 25-35° C. Nilotinib free base (15.0 g) was added slowly into the reactor at 25-35° C. under stirring. The reaction mass was stirred at 25-35° C. for 1-2 hrs. The reaction mass was passed through hyflow at 25-35° C. and washed with acetic acid (30 mL). The filtrate was charged into the reactor and ethyl acetate-HCl (8.98 g) was added slowly at 25-35° C. for 45-75 minutes. The reaction mass was maintained for 15-20 minutes at 25-35° C. and seed material (0.15 g, Form R6) was added. Ethyl acetate (300 mL) was slowly added at 25-35° C. for 90-150 minutes and the reaction mass was maintained at 25-35° C. for 60-90 minutes. The reaction mass was filtered on Agitated Nutsche Filter Dryer (ANFD) and washed with a mixture of acetic acid (15 mL) and ethyl acetate (15 mL) at 25-35° C. The material was dried in Roto Cone Vacuum Dryer at 110-120° C. under hot nitrogen to obtain the title compound.

The invention claimed is:

1. A process for preparing nilotinib hydrochloride Form R6 comprising the steps of:
    a) providing a solution of nilotinib free base in acetic acid;
    b) adding hydrochloric acid taken in an organic solvent to the solution obtained in step a);
    c) separating nilotinib hydrochloride Form R5; and
    d) drying at a temperature of about 100° C. to about 150° C. to obtain nilotinib hydrochloride Form R6.

2. The process of claim 1, wherein the organic solvent is selected from methyl acetate, ethyl acetate, propyl acetate, butyl acetate, methyl propanoate, ethyl propanoate, methyl butanoate and ethyl butanoate.

3. A process for preparing nilotinib hydrochloride Form R6 comprising the steps of:
    a) providing a solution of nilotinib free base in acetic acid and an organic solvent;
    b) adding hydrochloric acid to the solution obtained in step a);

c) separating nilotinib hydrochloride Form R5; and
d) drying at a temperature of about 100° C. to about 150° C. to obtain nilotinib hydrochloride Form R6.

4. The process of claim 3, wherein the organic solvent in step a) is selected from methyl acetate, ethyl acetate, propyl acetate, butyl acetate, methyl propanoate, ethyl propanoate, methyl butanoate and ethyl butanoate.

* * * * *